US010058098B2

(12) United States Patent
Grosman et al.

(10) Patent No.: US 10,058,098 B2
(45) Date of Patent: *Aug. 28, 2018

(54) METHOD FOR THE PROTECTION OF TREES

(71) Applicant: SYNGENTA PARTICIPATIONS AG, Basel (CH)

(72) Inventors: Donald M. Grosman, College Station, TX (US); David Cox, Greensboro, NC (US)

(73) Assignees: THE TEXAS A&M UNIVERSITY SYSTEM OFFICE OF TECHNOLOGY COMMERCIALIZATION, College Station, TX (US); SYNGENTA PARTICIPATIONS AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/106,886

(22) Filed: Dec. 16, 2013

(65) Prior Publication Data

US 2014/0107055 A1   Apr. 17, 2014

Related U.S. Application Data

(63) Continuation of application No. 13/489,097, filed on Jun. 5, 2012, now Pat. No. 8,633,167, which is a continuation of application No. 11/909,331, filed as application No. PCT/US2006/010145 on Mar. 21, 2006, now abandoned.

(51) Int. Cl.
*A01N 43/90* (2006.01)

(52) U.S. Cl.
CPC .................................. *A01N 43/90* (2013.01)

(58) Field of Classification Search
CPC ...................................................... A01N 43/90
See application file for complete search history.

(56) References Cited

U.S. PATENT DOCUMENTS 5,945,445 A   8/1999   Barringer et al.

FOREIGN PATENT DOCUMENTS

| JP | 8-208657 A2 | 8/1996 |
|---|---|---|
| JP | 10-152407 A | 6/1998 |
| JP | 2005-36807 A2 | 2/2005 |
| WO | 9520877 | 8/1995 |

OTHER PUBLICATIONS

Sclar, D. et al "Evaluation of new systemic insecticides . . . " J. Environ. Hort. (1996) vol. 14, No. 1, pp. 22-26.*
Berisford, C.W., U.E. Brady, R.F. Mizell, L.H. Lashomb, G.E. Fitzpatrick, I.R. Ragenovich and F.L. Hastings, 1980, "A Technique for Field Testing Insecticides for Long-Term Prevention of Bark Beetle Attack", J. Econ. Entomol. 73:694-607.
Dalusky, J.J., C.W. Berisford and P.B. Buch, 1990, "Efficacy of Three Injected Chemical Systems for Control of the Southern Pine Beetle", Georgia For. Comm. Ga. For. Res. Paper 83, 8p.
Grossman, D.M., W.W. Upton, F.A. McCook, and R.F. Billings, 2002, "Systemic Insecticide Injections for control of Cone and Seed Insects in Loblolly Pine Seed Orchards—2 Year Results", So. J. Appl. For. 26:146-152.
Strom, B.L., S.R. Clarke and P.J. Shea, 2004, Efficacy of 4-allyanisole-based Products for Protecting Individual Loblolly Pines From Dendroctonus Frontalis Zimmermann (Coleoptera:Scolytidae), Can. J. For. Res. 34:659-665.
Takai, K., T. Soejima, T. Suzuki and K. Kawazu, 2000, Emamectin Benzoate as a Candidate for a Trunk-Injection Agent Against the Pine Wood Nematode, *Bursaphelenchus xylophilus*, Pest Manag. Sci. 56:937-941.
Takai, K., T. Soejima, T. Suzuki and K. Kawazu, 2001, "Development of a Water-Soluble Preparation of Emamectin Benzoate and its Preventative Effect Against the Wilting of Pot-Grown Pine Trees Inoculated With the Pine Wood Nematode, *Bursaphelenchus xylophilus* ", Pest Manag. Sci. 57:463-466.
Takai, K., T. Suzuki and K. Kawazu, 2003a. "Development and Preventative Effect Against Pine Wilt Disease of a Novel Liquid Formulation of Emamectin Benzoate", Pest Manag. Sci. 59:365-370.
Takai, K., T. Suzuki and K. Kawazu, 2003b. "Distribution and Persistence of Emamectin Benzoate at Efficacious Concentrations in Pine Tissue After Injection of a Liquid Formulation", Pest Manag. Sci. 60:42-48.
Billings, R.F. 1980, Direct Control. Chapter 10 in The Southern Pine Beetle: R.C. Thatcher, J.L. Searcy, J.E. Coster, and G.O. Hertel, eds. USDA Tech. Bull. 1631, pp. 179-192.
Cane, James et al, "Susceptibility of Ips calligraphus (Germar) and Dendroctonus frontalis Zimmermann (Coleoptera Scolytidae) to coleopteran-active Bacillus thuringiensis, a Bacillus metabolite, and avermectin B-1", Canadian Entomologist, vol. 26(6), 1992, pp. 831-837 abstract only.

* cited by examiner

*Primary Examiner* — Leigh C Maier

(57) ABSTRACT

The present invention provides a method for the prevention/treatment of bark beetle and/or wood borer infestation of trees comprising treatment of the tree with a composition comprising a macroyclic lactone.

1 Claim, No Drawings

METHOD FOR THE PROTECTION OF TREES

This application is a continuation of copending U.S. application Ser. No. 13/489,097, filed on Jun. 5, 2012, which is a continuation of U.S. application Ser. No. 11/909,331, now abandoned, filed on Sep. 21, 2007, both of which are herein incorporated by reference in their entirety for all purposes.

The present invention relates to a method for the prevention/treatment of bark beetle and/or wood borer infestation of trees comprising treatment of the tree with a composition comprising a macroyclic lactone. In particular, the present invention relates to the use of emamectin benzoate in a method for the prevention/treatment of bark beetle infestation of trees.

A number of species of bark beetle cause a large amount of destruction to trees, in particular pine trees. Of these destructive species, the southern pine beetle (*Dendroctonus frontalis* Zimmerman) mountain pine beetle (*D. ponderosae* Hopkins), the western pine beetle (*D. brevicomis* LeConte), the spruce beetle (*D. rufipennis* Kirby), the Douglas fir beetle (*D. pseudotsugae* Hopkins), the pine engraver (*Ips pini* Say), the piñyon ips (*I. confuses* LeConte), the California five-spined ips (*I. paraconfusus* Lanier) and the Arizona five-spined ips (*I. lecontei* Swaine) are of particular note. Secondary bark beetles, including *I. avulsus* (Eichoff), *I. grandicollis* (Eichoff) and *I. calligraphus* (Germar), also are known to cause significant pine tree mortality in the southeastern United States. These beetles normally attack trees stressed by drought, lightening strikes, root disturbances, and other factors. In addition, wood boring cerambycid beetle larvae may also cause substantial damage to trees.

The beetles bore into the trees and mated adults dig galleries and channels under the bark. Eggs deposited in these channels hatch into larvae which feed on the cambium layer beneath the bark. The channels they form cut off the supply of water and nutrients and result in the death of the tree. In addition, the beetles may also carry fungi on their bodies which can germinate and spread within the trees—such fungi may also change the colour of the wood.

The southern pine beetle (SPB) (*D. frontalis* Zimmermann), is the most important pest of pine forests in the southern United States. Local and regional outbreaks of SPB cause severe economic losses on a nearly annual basis. Recently, an unprecedented outbreak extended across much of the southeast United States. During the period from 1999 to 2002, losses due to SPB-caused tree damage and mortality were estimated at over $1 billion (Report on losses caused by forest insects, Southern Forest Insect Work Conference, 2000, 2001, 2002 and 2003). The SPB does not just affect timber industry; it also has a significant impact on recreation, water, and wildlife resources as well as residential property. The urban/wildland interface is continuing to expand thus placing more high-valued residential trees at risk to SPB attack. The current abundance of susceptible trees and forests underlines the importance of the development of new methods to protect individual trees against SPB attack.

Protection of individual trees from SPB and *Ips* engravers has historically involved applications of chemical insecticides to the entire bole of the tree using hydraulic sprayers. Several products had been registered with the Environmental Protection Agency (EPA) for this use, including benzene hexachloride (BHC), Lindane®, fenitrothion (Pestroy®) and chlorpyrifos (Dursban®), but recently the use of the last of these, Dursban®, was withdrawn. In 2003, bifenthrin (Onyx®) was registered by EPA for use against several species of bark beetles including SPB and *Ips* engravers on ornamental plantings, but so far this product has not been made widely available to consumers and is not registered for use in forest situations. Even when available, insecticide spray applications have limitations. They are expensive, time-consuming, are a high risk for worker exposure and drift, and are detrimental to natural enemies (Billings 1980).

Systemic insecticides have been suggested as a potentially useful tool for protection of individual trees or forested areas. One of the first to be tested, acephate (Orthene®), was applied to foliage at two different rates (Crisp, Richmond, and Shea 1979 unpublished data, in Billings 1980). The treatments were reported to reduce SPB larval survival, but had no effect on eggs, pupae, callow or parent adults. A more recent study evaluated fenitrothion (Pestroy®) and a combination treatment of sodium N-methyldithiocarbamate (SMDC, Vapam®) plus dimethyl sulfoxide (DMSO) applied to bark hacks and dicrotophos (Bidrin®) applied by Mauget Injectors™ (Inject-a-icide-B®) to trees at the leading edge of SPB infestations (Dalusky et al. 1990).

Although tree mortality was not prevented by any of the treatments, dicrotophos was found to significantly reduce both egg gallery length and subsequent brood production. Because dicrotophos has a relatively high mammalian toxicity, it is not available to the general public. Oxydementon methyl (Metasystox-R) applied by Mauget injectors (Inject-a-cide®) is registered for use against several *Dendroctonus* and *Ips* species of bark beetles, but is not registered for SPB.

Due to the highly destructive nature of these beetles, new and more effective methods and compositions for protecting trees from their attack are always required.

Emamectin benzoate, an avermectin derivative, has shown systemic activity in pine and is highly effective against pine wood nematode, *Bursaphelenchus xylophilis* (Steiner & Buhrer) Nickle (Takai et al. 2000, 2001, 2003a, 2003b), and coneworm, *Dioryctria* spp. (Grosman et al. 2002), with protection lasting more than three years. Denim® (emamectin benzoate) is currently registered for use in foliar spray applications on cole crops against several lepidopteran species.

It has now been found that emamectin benzoate is surprising effective against bark beetles and wood borers.

Accordingly, the present invention provides a method for the prevention/treatment of bark beetle and/or wood borer infestation of trees comprising treatment of the tree with a composition comprising a macroyclic lactone.

A macrocyclic lactone compound is a compound having a ring in its chemical structure made up of twelve or more atoms. The atoms may be selected from carbon, oxygen, nitrogen or sulphur, preferably the atoms are carbon and oxygen. In an embodiment, the ring has up to 20 atoms. Examples include spinosad (737), avermectin and avermectin monosaccharide derivatives, such as abamectin (1), doramectin (25-cyclohexyl-5-O-demethyl-25-de(1-methylpropyl)avermectin $A_{1a}$; CAS RN 117704-25-3), emamectin (291), eprinomectin ((4"R)-4"-(acetylamino)-4"-deoxyavermectin $B_1$; CAS RN 123997-26-2), ivermectin (5-O-demethylavermectin $A_{1a}$ (i) mixture with 5-O-demethyl-25-de (1-methylpropyl)-25-(1-methylethyl)avermectin $A_{1a}$ (ii), CAS RN 70288-86-7 (70161-11-4+70209-81-3)) and selamectin ((5Z,25S)-25-cyclohexyl-4'-O-de(2,6-dideoxy-3-O-methyl-α-L-arabino-hexopyranosyl)-5-demethoxy-25-de (1-methylpropyl)-22,23-dihydro-5-(hydroxyimino) avermectin $A_{1a}$; CAS RN 165108-07-6), and milbemycin derivatives, such as milbemectin (557), milbemycin oxime ((6R,25R)-5-demethoxy-28-deoxy-6,28-epoxy-25-ethyl-5-

(hydroxyimino)milbemycin B mixture with (6R,25R)-5-demethoxy-28-deoxy-6,28-epoxy-5-(hydroxyimino)-25-methylmilbemycin B), moxidectin ((6R,23E,25S)-5-O-demethyl-28-deoxy-25-[(1E)-1,3-dimethyl-1-butenyl]-6,28-epoxy-23-(methoxyimino)milbemycin B; CAS RN 113507-06-5), and SI0009 (a milbemycin B mixture of 5-O-demethyl-28-deoxy-6,28-epoxy-25-methyl-13-[[(methoxyimino)phenylacetyl]oxy]-(6R, 13R, 25R)-(9CI) and 5-O-demethyl-28-deoxy-6,28-epoxy-25-ethyl-13-[[(methoxyimino)phenylacetyl]oxy]-(6R, 13R, 25R)-(9CI); CAS RN 171249-10-8 and 171249-05-1).

The natural Avermectins, which can be obtained from *Streptomyces avermitilis*, are referred to as A1a, A1b, A2a, A2b, B1a, B1b, B2a and B2b. The compounds referred to as "A" and "B" have a methoxy radical and an OH group, respectively, in the 5-position. The "a" series and the "b" series are compounds in which the substituent $R_1$ (in position 25) is a sec-butyl radical and an isopropyl radical, respectively. The number 1 in the name of the compounds means that carbon atoms 22 and 23 are linked by double bonds; the number 2 means that they are linked by a single bond and that the C atom 23 carries an OH group.

The pesticides, including spinosad, abamectin, milbemectin and emamectin, are described in the e-Pesticide Manual, version 3.0, 13th Edition, Ed. CDC Tomlin, British Crop Protection Council, 2003-04. The number following the compound name is the entry number given in the Pesticide Manual.

In one embodiment, the macrocylic lactone is a compound of formula (I):

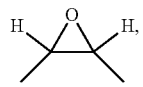

or a single bond and a methylene bridge of the formula

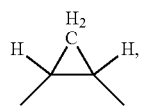

including, where applicable, an E/Z isomer, a mixture of E/Z isomers, and/or a tautomer thereof, in each case in free form or in salt form.

The compound of formula (I) may be in the form of tautomers. Accordingly, hereinbefore and hereinafter, where appropriate, the compound (I) is to be understood to include corresponding tautomers, even if the latter are not specifically mentioned in each case.

The compounds above are capable of forming acid addition salts. Those salts are formed, for example, with strong inorganic acids, such as mineral acids, for example perchloric acid, sulphuric acid, nitric acid, nitrous acid, a phosphoric acid or a hydrohalic acid, with strong organic carboxylic acids, such as unsubstituted or substituted, for example halo-substituted, C1-C4 alkane carboxylic acids, for example acetic acid, saturated or unsaturated dicarbox- (I)

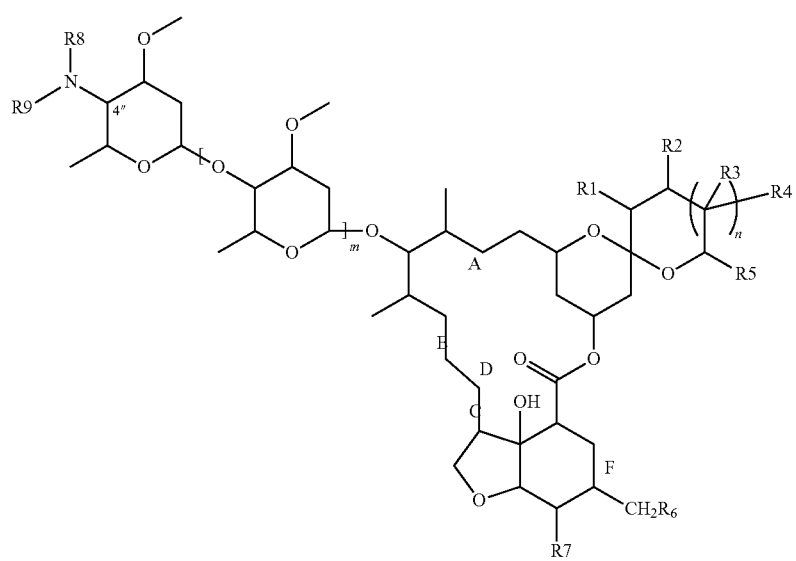

in which

R1 to R9 represent, independently of each other hydrogen or a substituent;

m is 0, 1 or 2;

n is 0, 1, 2 or 3; and the bonds marked with A, B, C, D, E and F indicate, independently of each other, that two adjacent carbon atoms are connected by a double bond, a single bond, a single bond and an epoxide bridge of the formula ylic acids, for example oxalic, malonic, succinic, maleic, fumaric or phthalic acid, hydroxycarboxylic acids, for example ascorbic, lactic, malic, tartaric or citric acid, or benzoic acid, or with organic sulphonic acids, such as unsubstituted or substituted, for example halo-substituted, C1-C4 alkane- or aryl-sulphonic acids, for example methane- or p-toluene-sulphonic acid.

Furthermore, compounds of formula (I) having at least one acidic group are capable of forming salts with bases. Suitable salts with bases are, for example, metal salts, such as alkali metal or alkaline earth metals salts, for example sodium, potassium or magnesium salts, or salts with ammonia or an organic amine, such as morpholine, piperidine, pyrrolidine, a mono-, di- or tri-lower alkylamine, for example ethyl-, diethyl-, triethyl-, or dimethyl-propyl-amine, or a mono-, di- or tri-hydroxy-lower alkylamine, for example, mono-, di- or tri-ethanolamine. In addition, corresponding internal salts may also be formed.

In view of the close relationship between the compounds of formula (I) in free form and in the form of their salts, any reference hereinbefore or hereinafter to the free compounds of formula (I) or to its salt is to be understood as including also the corresponding salts or the free compounds of formula (I) where appropriate and expedient. The same applies in the case of tautomers of compounds of formula (I) and the salts thereof.

In a particular embodiment, the invention is concerned with a compound of the formula (II):

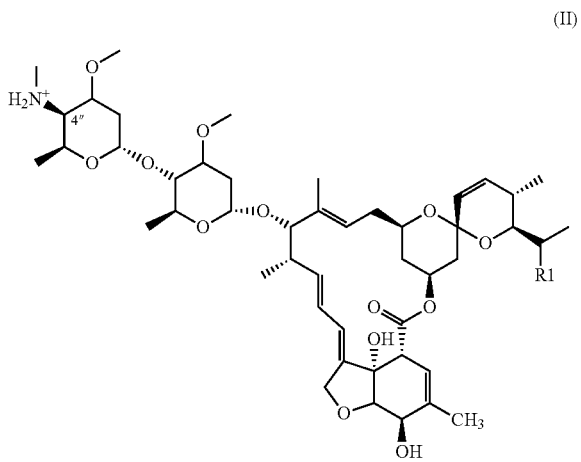

wherein R1 is methyl or ethyl.

This compound is known as 4"-deoxy-4"-N-methylamino avermectin B1a/B1b or emamectin. It is noted that when R1 is a ethyl group, the compound is the B1a form and when R1 is methyl, the compound is the B1b form. Generally, the compounds are used as a mixture of the two forms, B1a and B1b, since the structural differences are very slight and amount to the difference between sec-butyl group and an isopropyl group, and the two compounds have substantially the same chemical reactivity and biological activities. For convenience, the nomenclature B1a/B1b is employed to indicate the individual compounds and the mixture of such compounds. In particular, it is preferred that compositions contain 80% or more of the B1a component and 20% or less of the B1b component, more preferably 90% or more of the B1a component and 10% or less of the B1b component.

In particular, the present invention is concerned with the acid addition salt of the above compound. The acid may be benzoic acid, benzoic acid substituted with one, two or three substitutents selected from the group consisting of halogen, hydroxyl, carboxyl, C1-C6 alkyl and C1-C6 alkoxyl, benzene sulphonic acid, citric acid, phosphoric acid, tartaric acid or maleic acid. The preferred acid addition salts are formed with benzoic acid, salicyclic acid, gallic acid, benzenesulphonic acid an citric acid. The most preferred acid addition salt is that formed with benzoic acid and the compound comprising this salt is known as emamectin benzoate.

The active ingredient of the present invention may be applied to trees in any of the ways known in the art, e.g. spraying. However, the preferred method of application is via tree injection techniques and, in particular, via the Arborjet Tree IV™ microinfusion system (Arborjet, Inc. Woburn, Mass.).

The active ingredient may be formulated ways any one of a number of known ways and, in particular, may be formulated for use in tree injection methods. The active ingredient may be dissolved in a solvent to which a surfactant may be added and it can be applied together with further carriers, surfactants or other application-promoting adjuvants customarily employed in formulation technology.

Suitable solvents are: aromatic hydrocarbons, e.g. xylene mixtures or substituted naphthalenes, phthalates, such as dibutyl phthalate or dioctyl phthalate, aliphatic hydrocarbons, such as cyclohexane or paraffins, alcohols and glycols and their ethers and esters, such as ethanol, ethylene glycol, ethylene glycol monomethyl or monoethyl ether, ketones, such as cyclohexanone, strongly polar solvents, such as N-methyl-2-pyrrolidone, dimethyl sulphoxide or dimethyl-formamide, as well as vegetable oils or epoxidised vegetable oils, such as epoxidised coconut oil or soybean oil; or water. For tree injection methods, a solvent having a low viscosity is preferable.

Depending upon the nature of the active ingredient to be formulated, suitable surface-active compounds are non-ionic, cationic and/or anionic surfactants having good emulsifying, dispersing and wetting properties. The term 'surfactants' will also be understood as comprising mixtures of surfactants.

The surfactants customarily employed in formulation technology may be found in the following literature:
"McCutcheon's Detergents and Emulsifiers Annual" MC Publishing Corp., Glen Rock, N.J., 1988.
M. and J. Ash, "Encyclopedia of Surfactants", Vol. I-III, Chemical Publishing Co., New York, 1980-1981.

The invention will now be described with reference to the following examples:

EXAMPLES

The intent of the study was to evaluate the efficacy of systemic injections of emamectin benzoate in reducing success of pine bark beetle attacks on loblolly pine and determine the duration of treatment efficacy. As SPB populations were extremely low in Texas in 2004, *Ips* engravers beetles were used as indicator species.

Two 20-year-old, recently thinned loblolly pine plantations were selected on land owned by Temple-Inland Forest Products Corporation about 5 km south of Wells (Angelina County), Texas. Trees in one plantation were injected for use in a bolt study (Example 1). Trees in a 0.2 ha section of the second plantation were injected as part of a single-tree protection study (Example 2). A staging area also was set up in the second plantation where bolts from the first plantation were exposed to bark beetles and wood borers.

Example 1

Seventy-five loblolly pine trees, *Pinus taeda* L., 15-20 cm diameter at breast height (DBH), were selected in March 2004. Each treatment was injected into four cardinal points about 0.3 m above the ground on each of 15 trees in April (16$^{th}$-23$^{rd}$) using the new Arborjet Tree IV™ microinfusion system (Arborjet, Inc. Woburn, Mass.). The treatments included:
1) Emamectin benzoate (Denim®, 1.92% ai, Syngenta Crop Science)—Denim® was mixed 1:1 with methanol and applied at 18.6 ml solution per inch of tree diameter at breast height (DBH) (=0.2 g active per inch DBH).
2) Check (untreated)

After 1 (May 24), 3 (July 19) and 5 (September) months post-injection, 5 trees of each treatment were felled and two 1.5 m long bolts were removed from the 3 m and 8 m heights of the bole. The bolts were transported to a nearby plantation that was recently thinned and contained fresh slash material. Each bolt was placed about 1 m apart on discarded, dry pine bolts to maximize surface area available for colonization as well as to discourage predation by ground and litter-inhabiting organisms. To facilitate timely bark beetle colonization, packets of bark beetle pheromones (racemic ipsdienol+ lanerione combination, ipsenol or cis-verbenol; Phero Tech, Inc., Delta, BC, Canada) were attached separately to three 1 m stakes evenly spaced in the study area. Racemic ipsdienol and cis-verbenol were used with the second and third series of bolts deployed in July and September, respectively. The packets were removed after 2 weeks when signs of attacks (boring dust) were observed on most test bolts, signaling that naturally-produced pheromones were present.

Signs of beetle attack (boring dust) were visible on several bolts in just a few days after the bolts had been moved to the staging area and the pheromone baits deployed. Within 2 weeks, several *Ips* attacks and numerous cerambycid egg niches were evident on the bark surface of most bolts.

A clear panel of acetate (10 cm wide by 25 cm long) was attached to the center of each bolt after deployment of bolts to monitor arrival of bark beetles. The top surface of each panel was coated entirely with Stikem Special® trapping compound (Michel and Pelton, Emeryville, Calif.). The traps were left in place for two weeks.

Each series of bolts were retrieved about 3 weeks after deployment, after observing many cerambycid egg niches on the bark surface of most bolts. There was concern that if cerambycid larvae were allowed to develop too long, their feeding activity would obscure or obliterate the *Ips* galleries. Thus, each series of bolts were retrieved and stored temporarily in a TFS seedling cooler (~45° F.) to slow cerambycid development until the bolts could be evaluated.

In the laboratory, two 10×50 cm strips (total=1000 cm$^2$) of bark were removed from each bolt. Several measurements were made relating to construction of nuptial chambers and egg galleries and development of brood:
1) Number of unsuccessful attacks—penetration to phloem, but no egg galleries.
2) Number of successful attacks—construction of nuptial chamber and at least one egg gallery extending from it.
3) Number and lengths of egg galleries with brood galleries radiating from them.
4) Number and lengths of egg galleries without brood galleries.
5) Cerambycid activity, estimated by overlaying a 100 cm$^2$ grid over a portion of each bark strip and counting the number of squares overlapping area where cerambycid larvae had fed.

Treatment efficacy was determined by comparing *Ips* beetle attacks and egg gallery length and cerambycid feeding on treated and untreated bolts. The data were transformed by log$_{10}$(x+1) to satisfy criteria for normality and homoscedasticity (Zar 1984) and analyzed by GLM and the Fishers Protected LSD test using the Statview statistical program.

The number of *Ips* engraver beetles landing on individual bolts varied considerably but did not differ among the treatments for either height or series (Table 1). In contrast, the total number of attacks (nuptial chambers constructed) by male beetles often differed among the treatments. The number of attacks was not necessarily reflective of the success of the attack. As expected, in May, untreated bolts were heavily attacked. For all three series, nearly all nuptial chambers were successfully constructed on untreated bolts—with at least one egg gallery radiating from each nuptial chamber. In sharp contrast, on emamectin benzoate-treated bolts evaluated in May, most attacks were unsuccessful at the 3 m (79%) and 8 m (69%) heights and all (100%) attacks were unsuccessful at both heights in July and September. It appeared that nearly all attacks were aborted or the beetles died as soon as they penetrated into the phloem region. There were a few successful *Ips* attacks on one tree out of five in May, but these attacks were far fewer in number compared to check trees and were restricted to narrow strips on the bolt. In May, emamectin benzoate sharply reduced the total number (81% and 96%) and length (94% and 99%) of egg galleries at 3 m and 8 m, respectively, compared to check trees (Table 2). In July and September, emamectin benzoate completely prevented the construction of egg galleries in all bolts.

In May, cerambycid larvae were found to have fed upon 30% and 34% of the phloem area on untreated bolts taken from 3 m and 8 m, respectively, during the 3 weeks period between tree felling and bolt evaluation (Table 3). In contrast, very little larval feeding or development was found on emamectin benzoate-treated bolts. Overall, this treatment reduced feeding damage by 93% and 100% on bolts from 3 m and 8 m, respectively. Cerambycid larvae fed upon 23-25% and 9-14% of the phloem area on untreated bolts taken in July and September, respectively (Table 3). In contrast, both series of bolts exhibited no larval feeding or development on emamectin benzoate-treated bolts from 3 m. No colonization occurred at 8 m.

TABLE 1

Attraction to and attack success and gallery construction of Ips engravers beetles on loblolly pine bolts cut one, three and five months after trunk injection with emamectin benzoate

| Evaluation period | Bolt Height | Trt* | Mean # of Ips caught/Trap | Mean # of Nuptial Chambers Without Egg Galleries No. | | Mean # of Nuptial Chambers with Egg Galleries No. | | Mean Total # of Nuptial Chambers |
|---|---|---|---|---|---|---|---|---|
| | | | | No. | Total | No. | Total | |
| 1 Month Post-Injection (May) | 3 m | Emamectin | 3.8 a | 14.6 c | 78.5 | 4.0 a | 21.5 | 18.6 a |
| | | Check | 6.8 a | 0.0 a | 0.0 | 16.0 b | 100.0 | 16.0 a |
| | 8 m | Emamectin | 4.8 a | 9.0 c | 69.2 | 4.0 a | 30.8 | 13.0 ab |
| | | Check | 5.0 a | 0.2 a | 0.7 | 27.2 b | 99.3 | 27.4 c |
| 3 Months Post-Injection (July) | 3 m | Emamectin | 1.8 a | 11.0 b | 100.0 | 0.0 a | 0.0 | 11.0 ab |
| | | Check | 2.4 a | 0.8 a | 13.3 | 5.2 c | 86.7 | 6.0 a |
| | 8 m | Emamectin | 3.4 a | 8.4 c | 100.0 | 0.0 a | 0.0 | 8.4 b |
| | | Check | 2.8 a | 0.0 a | 0.0 | 3.8 b | 100.0 | 3.8 a |
| 5 Months Post-Injection (Sept.) | 3 m | Emamectin | 1.2 a | 3.8 b | 100.0 | 0.0 a | 0.0 | 3.8 a |
| | | Check | 1.6 a | 0.0 a | 0.0 | 5.2 b | 100.0 | 5.2 ab |
| | 8 m | Emamectin | 0.4 a | 4.4 b | 100.0 | 0.0 a | 0.0 | 4.4 a |
| | | Check | 2.2 b | 0.0 a | 0.0 | 7.8 b | 100.0 | 7.8 a |

* Means followed by the same letter in each column are not significantly different at the 5% level based on Fisher's Protected LSD

TABLE 2

Mean number and length of egg galleries constructed by Ips engravers beetles in loblolly pine bolts cut one, three and five months after trunk injection with emamectin benzoate

| Evaluation Period | Bolt Ht | Trt* | Number of Egg Galleries | | | | | Length of Egg Galleries | | | | |
|---|---|---|---|---|---|---|---|---|---|---|---|---|
| | | | Without Brood | | With Brood | | Total Galleries | Without Brood | | With Brood | | Total Length |
| | | | No. | % Total | No. | % Total | | cm | % Total | cm | % Total | |
| 1 Month Post-Injection (May) | 3 m | Emamectin | 10.0 a | 80.6 | 2.4 a | 19.4 | 12.4 a | 15.5 a | 50.5 | 15.2 a | 49.5 | 30.7 a |
| | | Check | 29.0 b | 44.1 | 36.8 c | 55.9 | 65.8 b | 114.8 b | 23.8 | 368.4 c | 76.2 | 483.2 c |
| | 8 m | Emamectin | 4.0 a | 95.2 | 0.2 a | 4.8 | 4.2 a | 12.3 a | 91.1 | 1.2 a | 8.9 | 13.5 a |
| | | Check | 30.0 b | 31.7 | 64.6 d | 68.3 | 94.6 b | 104.4 b | 17.7 | 483.8 c | 82.3 | 588.2 b |
| 3 Months Post-Injection (July) | 3 m | Emamectin | 0.0 a | | 0.0 a | | 0.0 a | 0.0 a | | 0.0 a | | 0.0 a |
| | | Check | 2.2 ab | 12.9 | 14.8 b | 87.1 | 17.0 c | 14.4 b | 9.2 | 142.0 b | 90.8 | 156.4 c |
| | 8 m | Emamectin | 0.0 a | | 0.0 a | | 0.0 a | 0.0 a | | 0.0 a | | 0.0 a |
| | | Check | 1.0 ab | 7.7 | 12.0 bc | 92.3 | 13.0 c | 2.4 ab | 1.5 | 153.6 c | 98.5 | 156.0 c |
| 5 Months Post-Injection (Sept.) | 3 m | Emamectin | 0.0 a | | 0.0 a | | 0.0 a | 0.0 a | | 0.0 a | | 0.0 a |
| | | Check | 2.8 c | 17.7 | 13.0 b | 82.3 | 15.8 c | 9.8 c | 6.1 | 150.6 b | 93.9 | 160.4 c |
| | 8 m | Emamectin | 0.0 a | | 0.0 a | | 0.0 a | 0.0 a | | 0.0 a | | 0.0 a |
| | | Check | 2.4 bc | 11.9 | 17.8 b | 88.1 | 20.2 c | 10.8 b | 4.6 | 223.4 c | 95.4 | 234.2 c |

TABLE 3

Cerambycid larval feeding in loblolly pine bolts cut one, three and five months after trunk injection with emamectin benzoate

| Bolt Height | Trt* | Percent Phloem Area Consumed by Larvae | | |
|---|---|---|---|---|
| | | 1 Month Post Injection (May) | 3 Months Post Injection (July) | 5 Months Post Injection (September) |
| 3 m | Emamectin | 2.2 a | 0.0 a | 0.0 a |
| | Check | 29.9 c | 23.0 bc | 9.3 c |
| 8 m | Emamectin | 0.0 a | 0.0 a | 0.0 a |
| | Check | 34.1 c | 24.5 b | 14.2 b |

*Means followed by the same letter in each column are not significantly different at the 5% level based on Fisher's Protected LSD Example 2

Loblolly pine, 15-20 cm DBH, were selected in the second plantation in March 2004. Each treatment (the same as those used in Example 1) was injected into four cardinal points about 0.3 m above the ground on each of 6 trees in April ($16^{th}$-$23^{rd}$) using the Arborjet Tree IV™ system. After 5 weeks post-injection (May 28), frills were cut with a hatchet into the sapwood between the injection points near the base of the tree. A cellulose sponge was inserted into each cut and loaded with 10 ml of a 4:1 mix of sodium N-methyldithiocarbamate (MS) (Woodfume®; Osmose, Inc., Buffalo, N.Y.) plus dimethyl sulfoxide (DMSO) (Aldrich Chemical) (Roton 1987, Strom et al. 2004). This method reduces resin to near zero in 1-2 weeks. The intent was to stress the tree and make it susceptible to attack by bark beetles without killing it.

Although the study area had adequate rainfall to maintain general tree health, the Vapam/DMSO treatment had the desired effect of stressing the trees. Resin weeping down the bark surface was the most visible sign of stress and this occurred on nearly 40% of study trees ($F=0.4487$; $df=4, 25$; $P=0.7723$). The treatments did not differ in proportion of trees with this stress symptom. Five of the six check trees showed signs of bark beetle attack (pitch tubes and boring dust) 2 weeks after the Vapam/DMSO treatment was administered. All study trees were evaluated about 4 weeks after the Vapam/DMSO treatment (=24 days after initial pheromone deployment).

Pheromone packets containing racemic ipsdienol+lanerione, ipsenol or cis-verbenol were attached (June 7) atop 3 m stakes evenly spaced in between and around the study trees to encourage attack by the three *Ips* engraver species. However, the initial results of the bolt trial suggested that encouraging *Ips calligraphus* (the largest and most common species) attack alone would allow for easier and more accurate measurements of beetle attack success. Thus, ipsdienol and cis-verbenol pheromone baits were deployed on all stakes on June $17^{th}$. The baits were changed every 4 weeks.

A clear panel of acetate (10 cm wide by 25 cm long) coated with Stickem Special® was attached 2 m high on standing trees after deployment of pheromone baits to monitor arrival of bark beetles. The traps were left in place for two weeks.

Three weeks after pheromone deployment (June 28), each tree was evaluated by marking a 30 cm section of bole at a height of 3 m. All visible *Ips* attacks and cerambycid egg niches were counted within the marked area. The number of trees with fading crowns also was recorded. Thereafter, the trees were evaluated weekly for crown fading. When mortality did occur, the trees were felled and two bolts taken and evaluated for attack success and gallery length as described in Example 1. All remaining trees were felled 66 days (August 9) after initial pheromone deployment when no additional trees had died for 3 weeks. Treatment efficacy was determined by comparing tree survival, beetle attacks and egg gallery length on treated and untreated bolts. As before, data were transformed and analyzed by GLM and the Fisher's Protected LSD test using the Statview statistical program.

All checks were heavily attacked by *Ips* and most had two or more cerambycid egg niches at 3 m (Table 4). In contrast, emamectin benzoate-treated trees had significantly fewer *Ips* attacks at the same height. Of the few *Ips* attacks that were found on these trees, nearly all appeared to have been unsuccessful based on the fact that the pitch tubes at the entrance holes were dry and brittle. None of the emamectin benzoate-treated trees had fading crowns (yellowing needles) (Table 6); whereas, two check trees exhibited fading crowns.

The study was discontinued after 66 days when no additional trees had faded in 20 days (Table 5). In the end, 5 of 6 (83%) of the check trees had died due to bark beetle attack. In contrast, all emamectin benzoate-treated trees survived. Evaluation of cut bolts showed that all trees had been attacked, but the emamectin benzoate-treated bolts had significantly fewer attacks at both heights than the check (Table 6). All attacks that did occur were completely unsuccessful. Emamectin benzoate-treated bolts had significantly fewer and shorter *Ips* egg galleries with and without brood and less area fed upon by cerambycid larvae compared to the check (Table 7).

In both examples, emamectin benzoate was highly effective in preventing successful attacks by *Ips* bark beetles and cerambycids one, three and five months after injection. On the bolts, at least, those male *Ips* that initiated attacks were either deterred or killed upon penetration into the phloem layer and exposure to the active ingredient. It is surmised that any pheromone production by males as they burrow through the bark was halted prematurely. Without these pheromones, very few, if any, females were attracted to the host material or entered the nuptial chamber to mate and begin construction of egg galleries. Even when females did arrive on a few of the logs of the first series and began construction of galleries, the galleries were very short and brood did not developed beyond the initial larval instars. Assuming that this scenario also occurred in the standing trees, the halting of pheromone production upon male contact with the phloem layer also halted the attraction of additional males, thus preventing the mass attack of the host tree.

The emamectin benzoate dose (0.2 g ai/inch of tree diameter) used in 2004 has been found to prevent successful attack by *Ips* engravers. If a lower dose were to be injected in trees at the leading edge of an active SPB infestations, the injected trees may serve as trap trees, i.e. allow successful mass attack, gallery construction and egg laying by adult SPB, but the larvae would not develop and no brood adults would be produced. If the treatment proved successful, it is conceivable that local populations of SPB would decline and the progression of the infestation would stop.

TABLE 4

Attraction and attacks by Ips engravers beetles and cerambycids to standing loblolly pine after trunk injection with emamectin insecticides

| Treatment | Mean # of Ips Caught/Trap | Mean # of Attacks/0.3 Bole Section at 3 m after 24 days | |
|---|---|---|---|
| | | Ips | Cerambycid |
| Emamectin | 1.2 a | 0.5 a | 0.8 a |
| Check | 6.5 b | 14.7 c | 4.3 a |

*Means followed by the same letter in each column are not significantly different at the 5% level based on Fisher's Protected LSD.

TABLE 5

Visible signs of mortality on standing loblolly pine after trunk injection with emamectin benzoate

| Treatment | Percentage of Trees With Fading Crowns After: | | | | | |
|---|---|---|---|---|---|---|
| | 24 days | 32 days | 39 days | 46 days | 52 days | 66 days |
| Emamectin | 0.0 a | 0.0 a | 0.0 a | 0.0 a | 0.0 a | 0.0 a |
| Check | 33.3 ab | 66.7 b | 83.3 b | 83.3 b | 83.3 b | 83.3 b |

*Means followed by the same letter in each column are not significantly different at the 5% level based on Fisher's Protected LSD

TABLE 6

Effects of emamectin benzoate insecticides on attack success and gallery construction of Ips engraver beetles on loblolly pine bolts cut after tree mortality or the end of the trial

| Bolt Height | Treatment | Mean # of Nuptial Chambers Without Egg Galleries | | Mean #of Nuptial Chambers With Egg Galleries | | Mean Total # of Nuptial Chambers |
|---|---|---|---|---|---|---|
| | | No. | % of Total | No. | Total | |
| 3 m | Emamectin | 3.0 ab | 100.0 | 0.0 a | 0.0 | 3.0 a |
| | Check | 3.2 ab | 32.8 | 6.5 b | 67.2 | 9.7 bc |
| 8 m | Emamectin | 1.3 ab | 100.0 | 0.0 a | 0.0 | 1.3 a |
| | Check | 0.8 ab | 12.2 | 6.0 bc | 87.8 | 6.8 b |

*Means followed by the same letter in each column are not significantly different at the 5% level based on Fisher's Protected LSD.

TABLE 7

Effects of emamectin on gallery construction of Ips engravers beetles and cerambycid larval development in loblolly pine bolts cut after tree mortality or at the end of the trial.

| | | Mean # of Egg Galleries | | | | | Mean Length of Egg Galleries | | | | | |
|---|---|---|---|---|---|---|---|---|---|---|---|---|
| | | Without Brood | | With Brood | | | Without Brood | | With Brood | | | |
| Bolt Ht | Trt* | No. | % of Total | No. | % of Total | Total Number | cm | % of Total | cm | % of Total | Total Length | Cerambycid Feeding Area |
| 3 m | Emamectin | 0.0 a | | 0.0 a | | 0.0 a | 0.0 a | | 0.0 a | | 0.0 a | 0.0 a |
| | Check | 17.2 b | 59.5 | 11.7 b | 40.5 | 28.8 b | 108.3 b | 48.0 | 117.2 b | 52.0 | 225.5 b | 3.6 b |
| 8 m | Emamectin | 0.0 a | | 0.0 a | | 0.0 a | 0.0 a | | 0.0 a | | 0.0 a | 0.0 a |
| | Check | 18.5 c | 40.5 | 27.2 b | 59.5 | 45.7 b | 91.0 b | 30.8 | 204.0 c | 69.2 | 295 b | 6.2 bc |

* Means followed by the same letter in each column are not significantly different at the 5% level based on Fisher's Protected LSD.

The invention claimed is:

1. A method for the reduction of wood borer beetle larvae feeding or development in the phloem area of living trees comprising treatment of the living tree with a composition comprising a macrocyclic lactone selected from emamectin benzoate, wherein the composition is applied to the living tree using an injection technique and wherein the composition is sufficient to reduce the number of wood borer beetle larvae to zero within the phloem area of the living trees within three months after the composition is applied to the living tree, and wherein the emamectin benzoate is applied at a rate of about 0.2 grams emamectin benzoate per inch diameter at a breast height of the living trees.

* * * * *